United States Patent [19]

Ray et al.

[11] Patent Number: 5,470,535
[45] Date of Patent: Nov. 28, 1995

[54] UNIVERSAL ZERO-HEADSPACE EXTRACTOR VESSEL

[75] Inventors: Carl Ray; J. Scott Coulter, both of Elko, Nev.

[73] Assignee: Xcel Industrial Group, Inc., Elko, Nev.

[21] Appl. No.: 208,790

[22] Filed: Mar. 9, 1994

Related U.S. Application Data

[63] Continuation of Ser. No. 875,242, Apr. 28, 1992, abandoned.

[51] Int. Cl.⁶ ................................................. B01L 11/00
[52] U.S. Cl. ..................... 422/101; 422/102; 73/864.62; 220/580; 92/98 R; 210/416.1
[58] Field of Search .................. 73/863.23, 863.25, 73/864.62; 210/416.1, 416.2, 416.3, 416.4, 416.5; 220/578, 580; 92/98 R; 422/101, 102

[56] References Cited

U.S. PATENT DOCUMENTS

| | | | |
|---|---|---|---|
| 632,830 | 9/1899 | Betzonick. | |
| 2,044,452 | 6/1936 | Terry | 137/153 |
| 3,886,800 | 6/1975 | Boehringer | 73/421.5 R |
| 4,224,858 | 9/1980 | Tsuchiyama | 91/410 |
| 4,604,110 | 8/1986 | Frazier | 55/74 |
| 4,862,754 | 9/1989 | Nimberger | 73/864.62 |
| 4,864,877 | 9/1989 | Ortiz et al. | 73/863.52 |
| 5,000,845 | 3/1991 | Solomon | 210/134 |
| 5,109,712 | 5/1992 | Nimberger et al. | 73/864.62 |
| 5,152,184 | 10/1992 | Schroeder | 73/863.11 |

Primary Examiner—Donald E. Czaja
Assistant Examiner—Milton I. Cano
Attorney, Agent, or Firm—Handal & Morofsky

[57] ABSTRACT

This invention provides a pressurizable zero-headspace extractor vessel useful in preparing mixtures of solid- and liquid-phase material for constituent analysis, for example for preparing environmental samples for analysis of toxic contaminants. The inventive extractor vessel has a sample chamber pressurizable either by gas or mechanically. The sample chamber is constructed with a removable liner of polytetrafluorethylene to be resistant to both organic an metallic contaminants and has a more robust pressure-resistant support housing, in which the liner is a snug fit, formed of a structural material such as high-density polyethylene. The invention also provides a rotary agitation apparatus for rotating such extractors or bottles end-over-end, in which apparatus the bottles are mounted in a manner which automatically centers them on the axis of rotation.

19 Claims, 7 Drawing Sheets

UNIVERSAL ZERO-HEADSPACE EXTRACTOR VESSEL

This application is a Continuation of application Ser. No. 07/875,242, filed Apr. 28, 1992, now abandoned.

TECHNICAL FIELD

This invention relates to a universal zero-headspace extractor vessel. More particularly it relates to such an extractor vessel designed for agitating a sample mixture comprising a solids-containing sample and an extraction liquid which extractor includes a separator or filtration means through which the sample mixture can be discharged under pressure. Solids are retained and the filtrate can be passed on for further processing. "Zero headspace" ensures that there is no air or gas above the sample mixture in the extractor, so that volatiles, gases or vapors, are restrained from escaping.

Such extractors find application in the examination of environmental wastes, especially in toxicity testing, and in mobility tests on contaminants and potentially hazardous wastes.

BACKGROUND

The Federal Register vol. 55 No. 61 pp. 11863–875 discloses a zero-headspace extractor vessel which provides for liquid/solid separation within the vessel and effectively or substantially precludes headspace.

The specification set forth in this Federal Register citation includes details of extraction methods as well as schematic drawings of typical specified apparatus. One such drawing is reproduced in FIG. 1 of the accompanying drawings where it is labeled "prior art".

The Federal Register prior art will be described in more detail hereinbelow. At this juncture, it will suffice to say that the zero-headspace extractor vessel shown comprises a cylinder which is divided, in a lengthwise sense, by a slidable piston into a sample chamber having an access port and a pressurizing chamber equipped with pressuring means. The access port is closable by solids-separation or filtration means and the pressurizing means is operable to drive the piston in the cylinder and press the sample mixture out through the filtration means where solids are retained and a liquid filtrate is expelled.

According to the drawing, the pressurization means can be a pressurized gas, controlled by a valve and the text states that some other zero-headspace extractors use mechanical pressure. Five such devices are referenced by manufacturer. A particular specification of interest in practicing the present invention calls for a vessel capacity of 500 to 600 ml., the ability to operate at a pressure of 50 psig, for a piston equipped with seals that do not leak at 50 psig and which will slide under an applied pressure of 15 psi, or less.

Because zero-headspace extractors are used to prepare specimens for sensitive tests of trace contaminants, there are precise requirements for their manufacture. Some of these requirements concern the materials of construction.

The Federal Register states that extraction vessels and filtration devices shall be made of inert materials which will not leach or absorb waste components. Specifically, "glass, polytetrafluoroethylene (PTFE) or type 316 stainless steel equipment may be used when evaluating the mobility of both organic and inorganic components. Devices made of high-density polyethylene (HDPE), polypropylene or polyvinyl chloride may be used only when evaluating the mobility of metals." Elsewhere, it is made clear that plastic materials, other than PTFE, cannot be used for determining organics.

Although not explicitly stated in this reference, stainless steel is not ideal for heavy metal determinations since it can leach contaminants such as chromium and nickel, from the vessel, into strong acids such as nitric that may be found in the sample. Furthermore, stainless steel is expensive and dense, rendering the extractor cumbersome and placing excess loads on tumblers or rotators used to agitate such vessels charged with sample mixtures. Stainless steel extraction vessels of the specified capacity of around 500–600 ml. can weigh as much as 15 lb. and usually are inconvenient to use, lacking a flat base on which they can be set for charging or discharging. Glass, especially the recommended borosilicate glass is excellent for inertness to contaminants, but is of course breakable. PTFE lacks structural strength and dimensional stability, is hard to shape and is expensive. (While the other polymers mentioned in the Federal Register reference are excellent lightweight structural materials, they suffer the limitation of being usable only for metal determinations.)

In developing this invention, applicants have undertaken the expense of a patent search of the prior art, which search revealed no relevant publications. By way of general background, the search revealed U.S. Pat. Nos. 632,830 (Betzonick), and 3,866,800 (Boehringer).

Betzonic employs a screw press to drive juice out of a sample of citrus fruit, through a crude, built-in sieve or filter. Boehringer discloses a gas-sampling device which provides a zero-headspace container for the gas for transport which container can be punctured to release the gas for analysis.

Two further U.S. Pat. Nos. disclosing zero headspace devices are 4,864,877 and 4,974,456 (both to Ortiz et al.). These patents, which have related disclosures, the latter being a divisional of the former, disclose zero-headspace sampling containers intended to meet EPA sampling requirements for liquids, not for multiphase samples, such as solvent-treated soil samples. Ortiz et al. do not disclose filtration means to retain sediment and do not appear to disclose pressurization of the containers. None of the constructions of these prior patents is suitable for meeting the objects of the present invention.

SUMMARY OFT HE INVENTION

The present invention satisfies a need. There is a need for a pressurizable zero headspace extractor vessel which can be used in preparing samples for tests for a full range of toxic contaminants, including volatile organics, metals, heavy metals and inorganics.

It is an object of the present invention to provide such a vessel.

It is another object of the present invention to provide such a vessel which can be advantageously used in preparing large numbers of test samples, providing economies of both equipment and labor.

A still further object is to provide such a pressurizable zero-headspace extractor vessel which is lightweight and economical.

Another object is to provide a pressurizable zero-headspace extractor vessel which has improved loadability and is robust.

Yet another object is to provide a zero-headspace extractor having a separable replaceable liner.

Accordingly, this invention fulfills these and other objects by providing a pressurizable zero-headspace extractor vessel useful in preparing multiphase sample mixtures for constituent analysis said sample mixtures containing solid-phase material and liquid-phase material. This extractor vessel has a collapsible sample chamber for said multiphase samples, a discharge port for egress of liquids from the sample chamber and a closing member movable to collapse said sample chamber and drive liquids out of said discharge port.

The extractor vessel further comprises pressurizing means to urge said closing member to move, solids-retaining filtration means to retain solid-phase material within the sample chamber as liquids are driven out and wettable surfaces in the vessel. These wettable surfaces are the surfaces contacted by the sample mixture during normal use of the vessel and are formed of an inert material which is chemically compatible with said sample mixture and with said constituents. The extractor vessel also comprises a structural member extending around said sample chamber and supporting at least one of said wettable surfaces to sustain a substantial working pressure in the sample chamber. The structural member is formed of a structural material which is non-compatible with at least one of said analyzable constituents.

The inert material can be a non-metallic, non-contaminating non-absorbent material, for example polytetrafluoroethylene.

Preferably, said structural material is a lightweight plastic material which can be selected from the group consisting of polypropylene, high-density polyethylene, poly vinyl chloride, and copolymers of any one of these polymers.

In a preferred embodiment, said structural members provide a casing extending generally around the sample chamber to provide three-dimensional support for said wetted surfaces.

Preferably the sample chamber is defined within a cylinder and said movable wall is comprised by a piston slidable within said cylinder. The structural members can comprise a tubular shell embracing said cylinder and heads, one head engaging each end of said shell and extending over the ends of said cylinder.

A manually operable screw means can be used to urge said movable wall, or piston, to pressurize said sample chamber.

BRIEF DESCRIPTION OF THE DRAWINGS

Some embodiments of the invention will now be described by way of example, and without limitation, with reference to the accompanying drawings, in which similar reference numerals indicate similar parts, even in different structural embodiments.

DETAILED DESCRIPTION OF THE PREFERRED EMBODIMENTS

Figure 1:
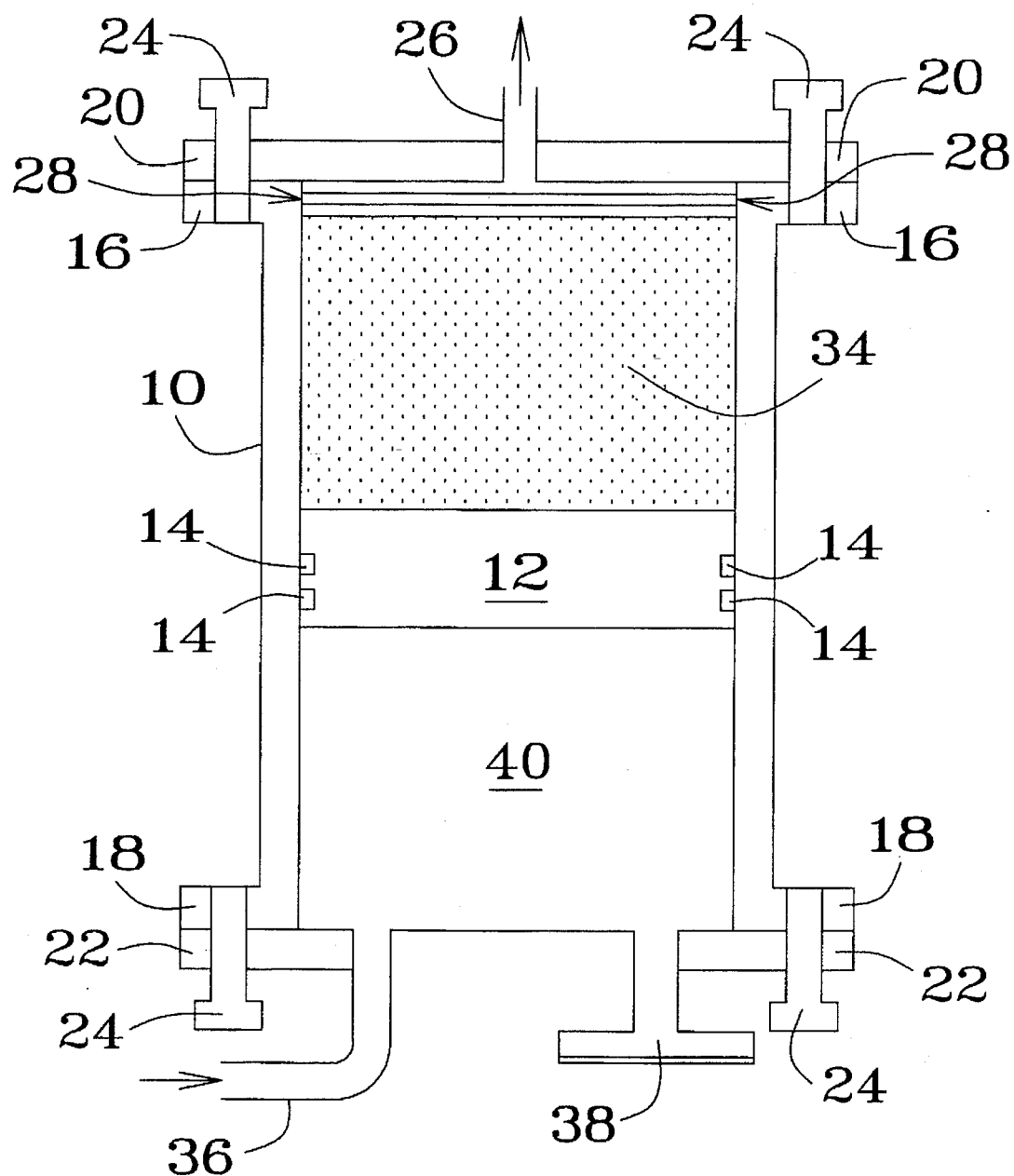
FIG. 1 of the drawings is a diametrical vertical section through a right-cylindrical prior art zero-headspace extractor vessel, the symmetrical vertical surfaces of which are circular-sectioned.

The prior art zero-headspace extractor vessel shown in FIG. 1 comprises an open-ended cylinder 10 in which a piston 12 is slidable, in sealing engagement with the cylinder 10 maintained by sealing rings 14. The upper and lower ends of the cylinder 10 have peripheral lips 16 and 18 respectively to which a top flange 20 and a bottom flange also respectively, are removably secured by bolts 24.

All directions and dispositions used in this description are with respect to the geometry of the cylinder 10 in an upright or vertical position., The top flange 20 carries a central discharge port 26 which can include or connect with an inlet/outlet valve and cooperates with the cylinder 10 to hold a filter 28 in the top end of the zero-headspace extractor vessel. The filter 28 can comprise a filter disk, typically of glass fiber, sandwiched between upper and lower support screens. These components close the upper end of the cylinder 10 and define with the cylinder 10 and the piston 12 a pressurizable sample chamber 34.

The bottom flange 22 carries a gas or compressed air line 36, which can connect with or include, a pressure control valve, and carries a pressure gauge 38, which components are used to charge a pressure chamber 40 on the lower side of the piston 12.

In use, the sample chamber 34 is charged with a sample mixture with the top flange 20 and the filter 28 removed. The samples for which this zero-headspace extractor vessel is intended are ones having some solids material content, for example environmental waste products subject to toxicity tests. Typically, the samples are mixed with an extraction solvent and this can be done in the sample chamber 34. Following the relevant Federal Regulations, the sample mixture is agitated, after reassembling the top flange 20 and the filter assembly, with filter disks 28, to the cylinder 10, by turning the zero-headspace extractor vessel end over end in a rotary agitation apparatus. A specified rotation rate for toxic waste samples is 30 rpm. ±2 rpm.

After agitation, filtrate is discharged through the port 26 under pressure applied from the pressure chamber 40, solids being retained on the filter disk 28. The Federal Register defines as solids, any material so retained. A specified operating pressure is 50 psig, which an empty zero-headspace extractor vessel must hold for at least 30 minutes. In such an empty vessel, the piston 12 is required to be movable under a pressure of 15 psig or less. These two requirements place tight constraints on the construction of the seals 14, for which a sealing material known as Viton (a trademark of Dupont) is specified.

The materials of construction of this prior art device are as set forth above, different materials being required for different tests and stainless steel being used for determining organics, providing a rather heavy and cumbersome vessel. Also, as stated above, it is known from the Federal Register reference to use either mechanical or gas-pressure means to pressurize the piston 12 and such devices are commercially available.

Figure 2:
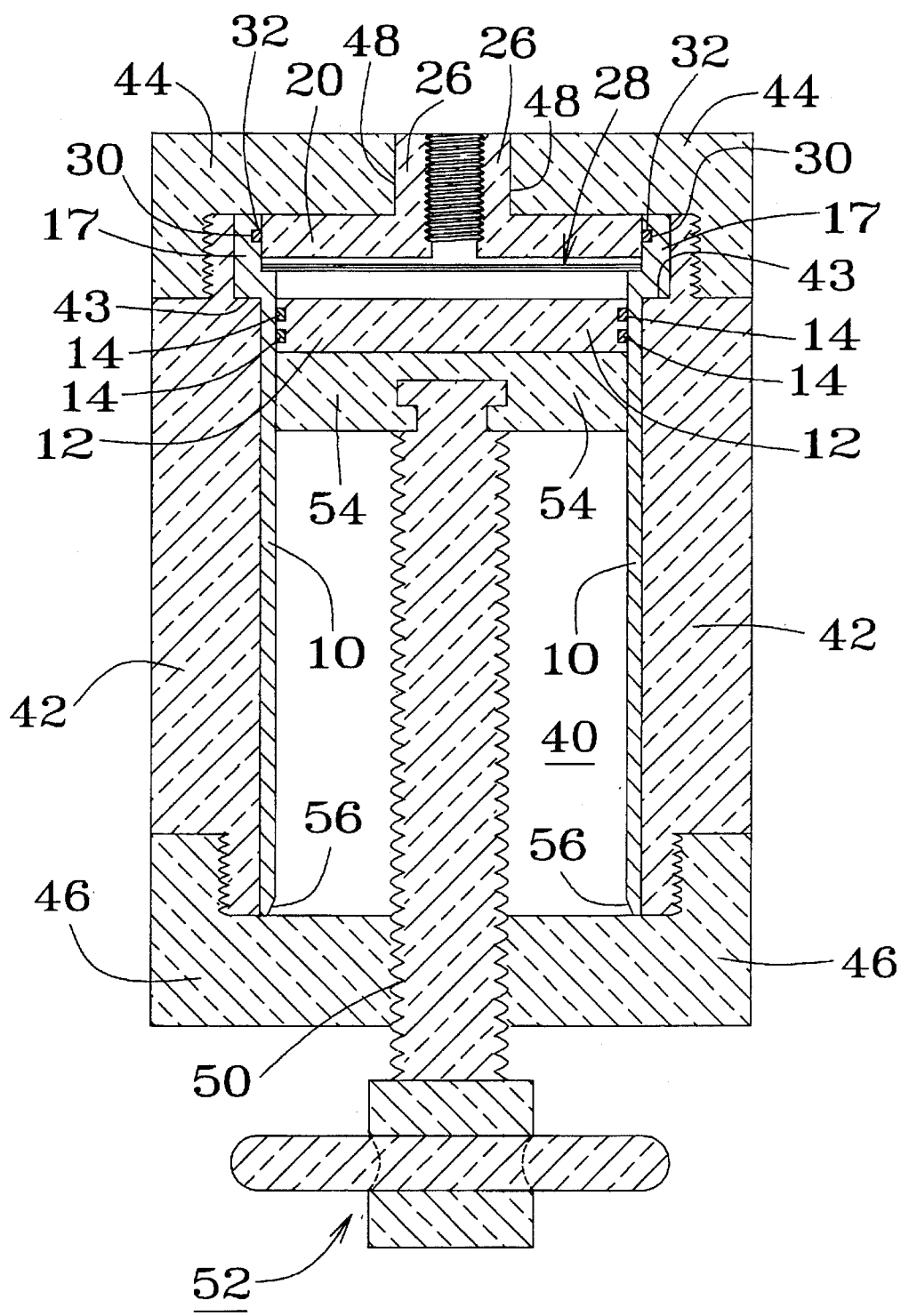
FIG. 2 of the drawings is a view similar to FIG. 1 of one embodiment of a zero-headspace extractor vessel according to the invention which is similarly a right-cylindrical vessel with circular-sectioned vertical surfaces and a mechanically driven piston within the vessel.

Referring now to FIG. 2, a zero-headspace extractor vessel according to the present invention also comprises a cylinder 10, a piston 12 equipped with sealing rings 14, and an enlarged diameter portion 17 of the cylinder 10 rather than the peripheral lip 16 of the prior art. The inventive extractor vessel further comprises a closing member in the form of a top flange 20, a discharge port 26, which in this inventive embodiment is threaded, a filter 28, a sample chamber 34 and a pressure chamber 40. The enlarged diameter 17 of the cylinder 10 provides a seat for the filter 28 and the end flange 20.

These components are individually self-supporting and their sample-mixture wettable surfaces are formed of a self-supporting material which is non-contaminating, inert to all the intended constituents to be analyzed, or to test samples, and to test and extraction reagents, and is preferably non-metallic to be suitable for testing for metals. In other words the wetted material is chemically compatible with the sample material or waste, and the constituents to be analyzed. Furthermore, the wetted material should not absorb the analysis constituents; which can be an important problem with regard to organic constituents, especially volatile ones. In this inventive construction, although self-supporting, the cylinder 10 is of light construction to be economical and replaceable and is not robust enough to sustain an adequate working pressure without deformation and leakage.

A particularly inert, stable, non-porous material is required for the wetted surfaces of the zero-headspace extractor, and this material needs also to be readily formable and mechanically stable. While plastics have many structurally desirable properties and are relatively inert, as described above, most plastics do have some unacceptable activity under the conditions specified.

The only plastic material currently approved by the EPA for the wetted surfaces is polytetrafluoroethylene (PTFE), for example TEFLON (Dupont). However, other plastics materials are known which can satisfactorily meet the conditions set forth above. Such materials can generally be described as fluorinated organic structural polymers of low surface porosity with little affinity for volatile agents. While expensive, some fluorination is effective to reduce the reactivity of the polymer and to ensure that the plastic does not bring its own volatiles, such as traces of monomer ingredients, to the extraction vessel, as a potential source of contamination.

Some such types of fluorinated polymer are fluorinated polymers and copolymers of alkylenes and alkoxylenes as well as of chlorinated alkylenes and alkoxylenes. Some examples are perfluoroalkoxylene (PFA, DuPont), fluorinated ethylene propylene (FEP, DuPont), HYPALON (trademark, DuPont) ethylene tetrafluoroethylene (Tefzel, DuPont) and a copolymer of chlorotrifluoroethylene known as KEL-F (trademark 3M) Corporation). Further desirable characteristics of these fluorinated polymer materials are that they do not readily degrade or leach out contaminants into the extraction solvent.

This fluorinated material, PTFE in a preferred embodiment, can be used for the cylinder 10 which, as shown, is constructed integrally with the enlarged diameter portion 17, for the piston 12 and for the top flange 20 which is formed integrally with the discharge port 26. The filter 28 can be glass fiber, which is specified by the EPA and can be multi-component to provide support.

Such chemically stable materials are not per se suitable for the load-bearing structure of a leakproof, pressurizable zero-headspace extractor because PTFE, for example, does not have adequate dimensional stability for tight seals, is hard to mold into structural shapes and is expensive: PTFE is usually supplied in sheets or tubes and, because of its high softening point (about 287° C.) and high melt viscosity, is often shaped by expensive sintering techniques. Accordingly, a piston and cylinder formed of PTFE would either be very expensive or would not seal adequately because the cylinder diameter would expand or deform under operational pressures of the order of 50 psig.

Additionally to the prior art construction of FIG. 1, the enlarged diameter portion 17 has a peripheral recess 30 in which is seated an O-ring seal 32, preferably also formed of Viton. The seal 32 is engageable by the end flange 20 and serves to retain liquids in the cylinder 10, to retain volatiles and to maintain pressure. If desired, the flange 20 and the enlarged end portion 17 of the cylinder 10 can be tapered for an improved closing action and to make a better seal.

In an alternative construction (not shown), the enlarged diameter portion 17 is deprived of side walls and comprises a lip in which the recess 30, with the seal 32 seated therein, faces upwardly and the disc-like end flange 20 extends outwardly over the seal 32 which is thus axially compressible, referring to the axis of the cylinder 10.

To overcome the problems of employing for the wetted surfaces a material which is chemically compatible with a diversity of types of sample and reagents, the present invention provides, in the embodiment shown in FIG. 2, a thin-walled cylinder 10, which although comprising a self-supporting integral structural element, is not capable of sustaining the desired working pressure by itself. To support the thin-walled cylinder 10, the invention further provides an external support casing for the cylinder 10 to ensure that it can sustain the desired working pressure, which requires a good seal between the piston 12 and the cylinder 10. This support casing can be comprised of several elements and can extend around the top flange 20, the enlarged diameter portion 17 and the open lower end of the cylinder 10 to be a snug fit around these elements.

One embodiment of such a support casing is shown in FIG. 2 and comprises a tubular shell 42 with male-threaded ends and two female-threaded end caps engageable therewith. The female-threaded end caps comprise a discharge end cap 44 at the upper end of the cylinder and a screw end cap 46 at the lower end of the cylinder. The upper end of the shell 42 has an internal cutout 43 to accommodate the enlarged diameter portion 17 of the cylinder 10 and support it. Discharge end cap 44 has a plain central opening 48 that is a close fit over the discharge port 26. Screw end cap 46 has a threaded central opening 50 to receive a thumbscrew 52. The end caps 44 and 46 can be provided with finger grips, or adapted to receive a wrench to facilitate tightening onto the shell 42 and removal therefrom. These optional features are not shown.

The material of the support casing could be stainless steel, but the construction of this invention makes it possible to employ a more advantageous lightweight plastic, for example polypropylene. Other moldable structural plastics can be used including high density polyethylene, polyvinyl chloride and copolymers of either. Clearly, there is a wide class of synthetic polymer materials that are suitable, the constraints being less severe than those on the wetted materials. Some further examples are ultrahigh molecular weight polyethylene, chlorinated polyvinyl chloride, acrylonitrile butadiene styrene copolymer (ABS), polyvinylidene fluoride (e.g. KYNAR, Pennwalt Corp.) and polyacetal plastics (e.g. DELRIN, DuPont).

Such structural materials are incompatible with at least one of the analyzable constituents of the sample mixture, or the extraction fluid in that the structural material could confuse the analysis thereof. For example, a volatile organic, such as benzene may have components absorbable by polypropylene resulting in a low reading on a benzene-contaminated sample and perhaps a false positive for a benzene-free sample, were polypropylene to be used for a wetted sample chamber surface.

As shown by the relative proportions used in FIG. 2, the shell 42 and end caps 44 and 46 are substantially more robust and thicker than the cylinder 10, when rendered in plastic, perhaps two or three times as thick.

The zero-headspace extractor vessel shown in FIG. 2 further comprises mechanical means to drive the piston 12 and pressurize the sample chamber 34 in the form of a detachable screw assembly comprising a thumbscrew 52 threaded into the mating opening 50 in lower end cap 46. Thumbscrew 52, which could employ any suitable manually operable device to turn it, for example a cross bar, carries at its inner end a drive plate 54 which backs the piston 12 to apply pressure to it in an even manner.

The cylinder 10 bears an internal chamfer 56 at its lower end which facilitates loading of the piston 12 into cylinder 10 noting that the sealing rings 14 can be expected to protrude laterally beyond the internal cylinder diameter. Chamfer 56 also serves as a guide for the drive plate 54, which is inserted frequently into the cylinder 10, speeding the operation.

The inventive zero-headspace extractor vessel shown in FIG. 2 is designed to be used in accordance with the methods of the Federal Register citation above and to provide some novel advantages as well as some advantageous improvements to that method. It is easier to open and close, requiring manipulation of a single, easily gripped end cap 44 rather than a plurality of closure screws 24 (FIG. 1).

Once opened by removal of the top end cap 44 and the filter 28, the zero-headspace extractor vessel can be charged with a sample mixture through the upper end of cylinder 10, closed by replacing the end cap 44 and the filter 28 and then the piston 12 can be screwed upwardly to remove air and zero out the headspace. The novel design of the invention provides for closure of the top end cap 44 to press flange seal 32 into tight engagement with top flange 20 ensuring an effective seal preventing leakage of the sample mixture. This is achieved because pressure is applied evenly around the seal and because the enlarged diameter portion 17 and the top flange 20 are firmly sandwiched between the end cap 44 and the shell 42, within the cutout 43.

Once closed, the shell provides excellent lateral support for the cylinder 10 ensuring that it can take the pressure needed to expel the sample mixture filtrate without leakage past the piston 12. At the lower end the stable threaded end cap 46, solidly screwed onto the shell 42 provides good support for the thumbscrew 52.

Further advantages of the inventive construction when rendered in plastic are that it is lightweight, easy and comfortable to handle and provides some heat insulation of the sample mixture to hold it at a preferred temperature.

Another advantage is that it can be easily loaded or unloaded by removing the thumbscrew 52 in an assembly with the bottom end cap 46 and the back plate 54 (with the zero-headspace extractor vessel inverted, of course). The thumbscrew 52 preferably includes means to withdraw the piston 12 at the same time. This provides easier access than having to remove the filter 28. Also, and importantly, the sample mixture, once charged into the sample chamber 34 can be quickly covered to eliminate any headspace and minimize exposure of the sample mixture to air, by lowering the thumbscrew and piston into place and quickly screwing the lower end cap 46 onto the shell 42. This can be facilitated by appropriate pre-positioning of the thumbscrew 52 in the end cap 46.

Figure 3:
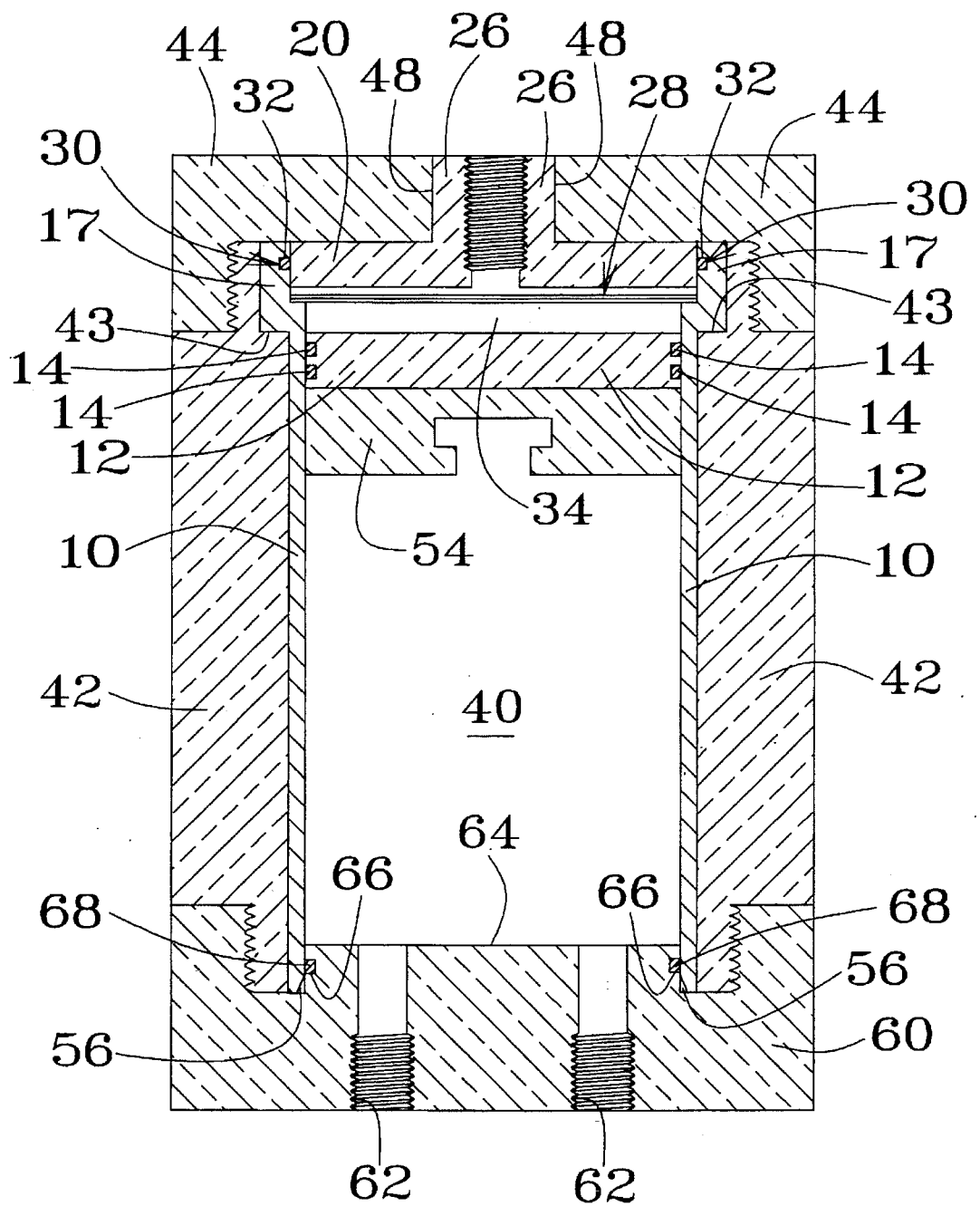
FIG. 3 of the drawings is a view similar to FIG. 2 of another embodiment of a zero-headspace extractor vessel according to the invention which is similarly a right-cylindrical vessel with circular-sectioned vertical surfaces and has a gas-pressure driven piston within the vessel.

The embodiment of FIG. 3 shows a zero-headspace extractor in which the piston is driven by gas pressure. Gas pressure devices are preferred by some operators for speed: They are quicker and easier to pressurize to the required end pressure. However, gas-pressure zero-headspace extractors require a cumbersome and often expensive air pressure source and are not, of course, suitable for field use. Accordingly, there is a market for both mechanical and gas-pressure zero-headspace extractors, according to the needs and preferences of the user.

As is shown in FIG. 3, read in conjunction with FIG. 2, the invention provides both types or models of zero-headspace extractor with maximum parts: interchangeability and a remarkable economy of part numbers. Thus, the mechanically or manually pressurized device of FIG. 2 can readily be converted for gas pressure operation by replacing the thumbscrew 52 and screw end cap 46 with a pneumatic end cap 60. Note that piston drive plate 54 is removable from the thumbscrew 52 and serves a similar driving function in the gas pressure zero-headspace extractor of FIG. 3. The pneumatic end cap 60 is a modified version of screw end cap 46. The pneumatic end cap 60 is equipped with two threaded air connector openings 62 in place of the thumbscrew opening 50, and has a raised central circular land 64 provided with a peripheral recess 66 in which a further O-ring seal 68 is seated, to maintain gas pressure behind the piston drive plate 54. Preferably, for sealing efficiency, the seal 68, which could be a pair of seals if desired, is also a Viton seal. One opening 62 is for an air pressure line with an adequate supply, for example 50 to 100 psig, and the other opening 62 is for a pressure relief valve or regulator and pressure gauge, to control the desired end pressure.

Operation and use of the gas-pressure zero-headspace extractor embodiment of FIG. 3 is similar to that of FIG. 2 except that the piston 12 is driven upwardly by opening a valve in the air supply line rather than turning the thumbscrew 52. Such a valve and air-line connector (not shown) can be mounted in one of the openings 62.

The efficient conversion that can be effected between the mechanically pressurized embodiment of FIG. 2 and the gas-pressurized, or pneumatic embodiment of FIG. 3 is advantageous from the points of view not only of manufacturing economy, but also in marketing and to the end user who can economically and quickly convert one and the same general zero-headspace extractor assembly between the two forms of piston drive, according to his needs.

The discharge port 26 can be equipped with a small discharge valve and connector (not shown) to seal the zero-headspace extractor for agitation, especially for end-over-end agitation, while adequate pressure is maintained on piston 12 to zero out any headspace.

An important advantage of the invention is that it provides for disposability of wear components. The cylinder 10 can readily be scratched and damaged by abrasive sample components, for example soil samples. Although resistant, it may also become contaminated, perhaps as a result of such mechanical damage, for example by very adhesive sample components such as paints or sticky oils. In the lightweight, thin-walled cylinder embodiment of the invention, which constitutes a removable separable liner, replacement is easy and economical. Clearly, the zero-headspace extractor of the invention may be marketed as a kit including a plurality of such disposable cylinders or separable liners, for example three, six or twelve. Similar considerations apply to the piston 12 and any other wetted components, which can also be supplied in such a kit in small numbers for disposability.

Such a kit can further include one each of the screw end cap 46 and thumbscrew 52 along with the pneumatic end cap 60 and any associated hardware for operation of the zero-headspace extractor either mechanically or pneumatically.

All the seals 14, 32, and 68 have a radial direction of compression for longevity and tightness, and the construction is such as to arrange that they seal against outward flow in an axial rather than a radial direction. Each of these three seals is firmly clamped between the shell 42 and rigid internal components in a solid, tight-sealing manner. The end seals 32 and 68 are tightened by closure of the end cap 46 or 60, with the mechanical advantage of the screw action and avoiding any need for wrench- or heavy hand-tightening of the end caps 46 or 60 to make an axial seal.

A zero-headspace extractor constructed generally as shown and described in FIG. 2 or FIG. 3 is substantially lighter and less cumbersome than known stainless steel models. For example, a zero-headspace extractor with a capacity of about 500–600 ml. can weigh less than 10 lb., compared with an example of 15 lb. for stainless steel, and a preferred embodiment weighs as little as six or seven pounds.

Furthermore, being designed with flat end faces, provided on the exterior surfaces of the end caps 46 and 60, as may be seen in the drawings, a zero-headspace extractor according to this invention can readily be set on a flat work surface. Alternatively, where it has downwardly projecting devices, such as the thumbscrew 52 or a relief valve, the zero-headspace extractor of preferred embodiments can be set on an appropriately slotted surface.

Figure 4:
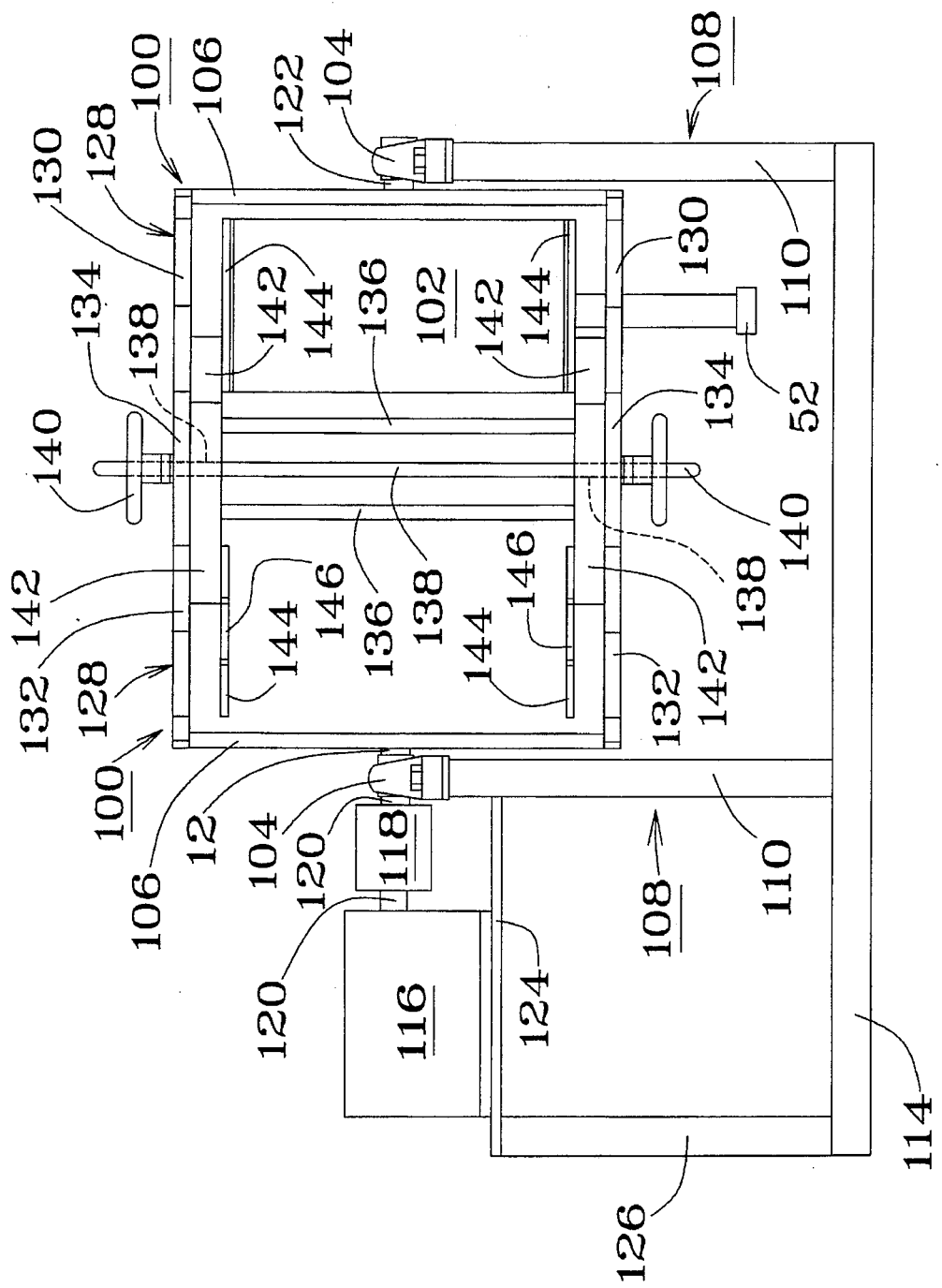
FIG. 4 is a side elevational view of a rotary agitation apparatus suitable for agitating bottles or zero-headspace extractors such as those shown in FIGS. 1 to 3.
Figure 5:
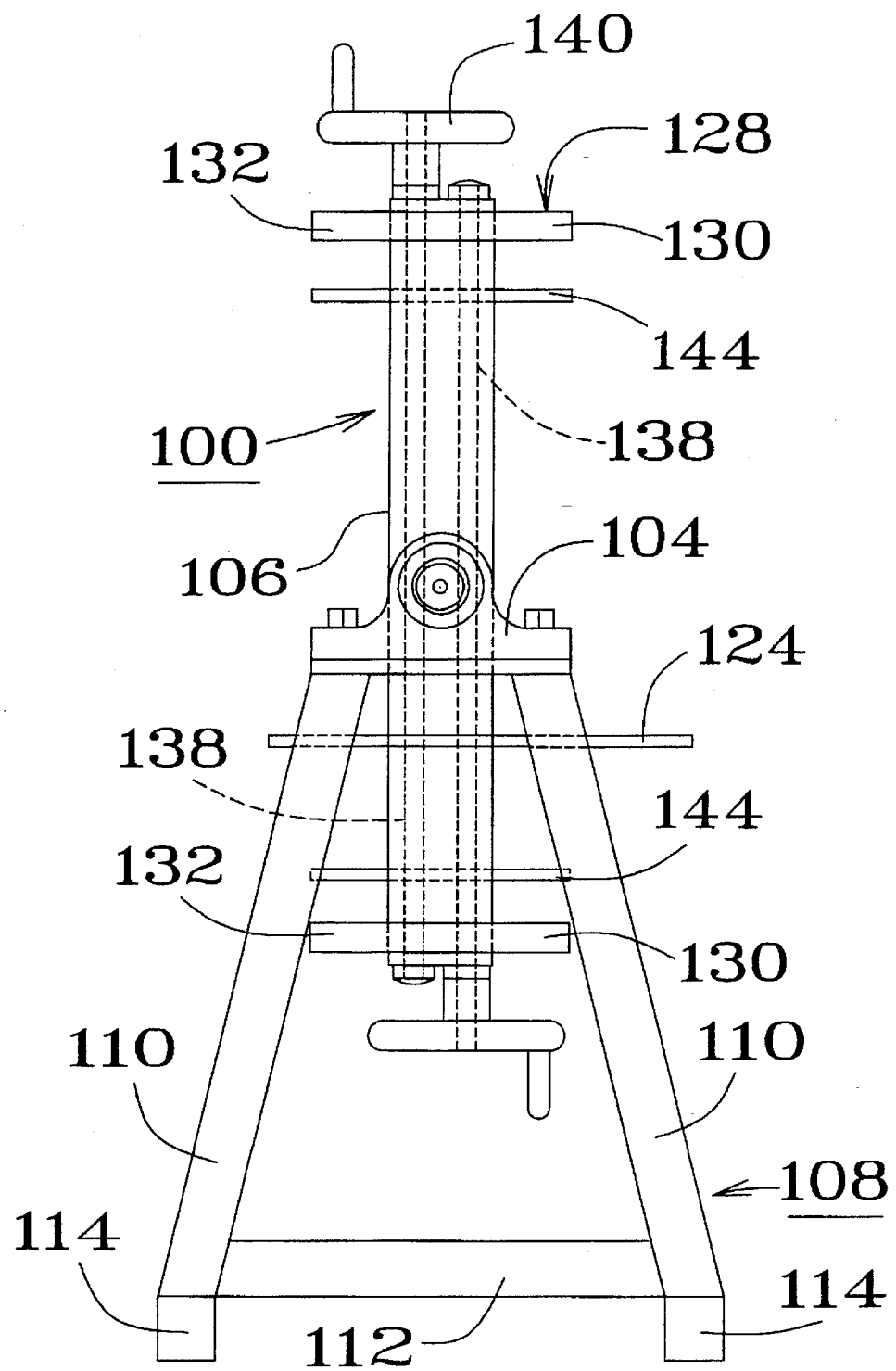
FIG. 5 is a right-hand end elevational view of the apparatus of FIG. 4 with some components omitted for clarity.
Figure 6:
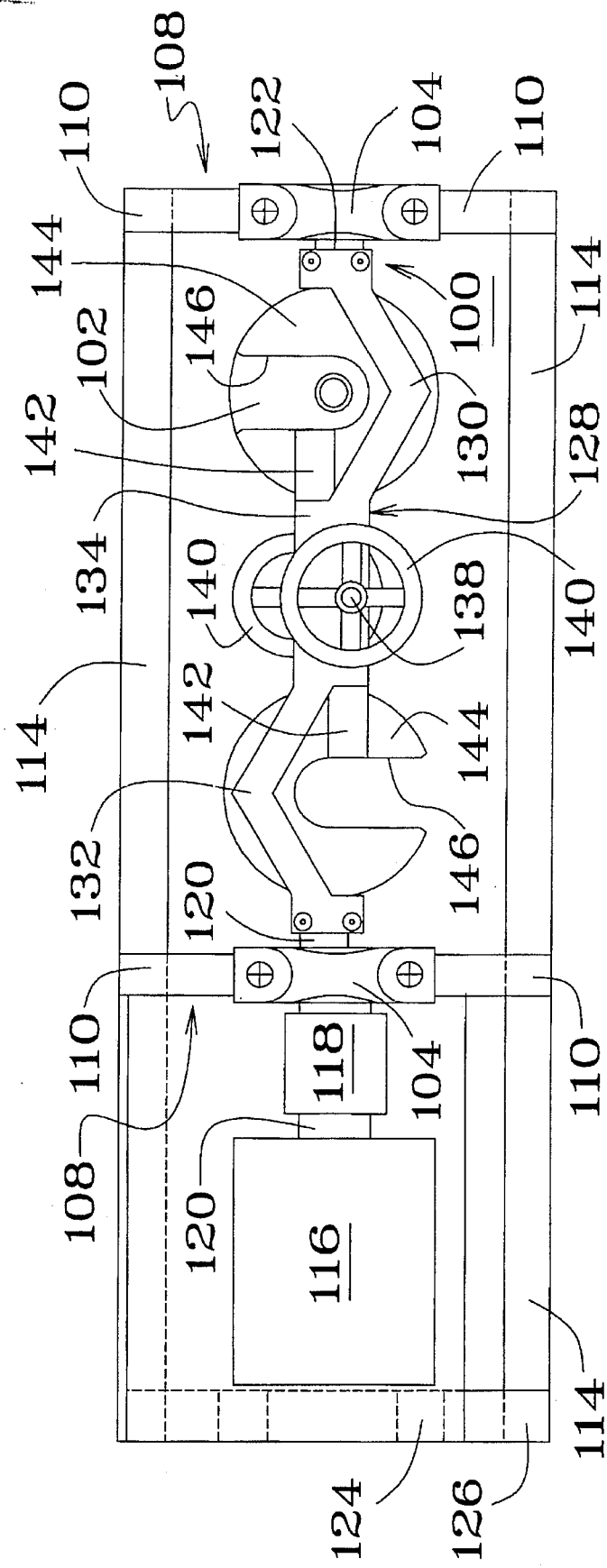
FIG. 6 is a top plan view of the apparatus of FIG. 4.

Referring now to FIGS. 4 to 6, another aspect of the invention provides a rotary agitation apparatus which can be used to rotate elongated objects, herein called "bottles" for the sake of convenience, in an end-over-end manner. In particular, this rotary agitation apparatus is designed to agitate zero-headspace extractors, such as those described with reference to FIGS. 1 to 3, in accordance with the requirements of the aforesaid Federal Register. The term "bottle" is used in a general sense to include such zero-headspace extractors as well as other elongated objects requiring end-over-end rotation, whether or not they are hollow and loaded with contents. However, it is envisaged that the rotary agitation apparatus of this aspect of the invention will primarily be used for rotating bottles with liquid or semi-solid contents, and especially zero-headspace extractors such as those shown in FIGS. 2 and 3.

For adequate efficiency, it is necessary to rotate a plurality of such bottles about a common axis with a single motor. One problem encountered in doing this is that of balancing the centrifugal forces developed by bottles of different sizes. Further problems arise in accommodating appendages to the bottles that unduly increase their length and will extend radially of the axis of rotation during rotation.

It would also be desirable to have a bottle rotator capable of meeting the requirements of the Federal Register which can quickly and easily be loaded with such bottles and which provides for speedy unloading. The actual requirement of the Federal Register is in fact very simple, namely "Any device that rotates the extraction vessel in an end-over-end fashion at 30 ±2 rpm is acceptable." Shown schematically in the Federal. Register is a simple device in which four extraction vessels are aligned along an axis of rotation in an elongated block-like holder through which they extend transversely. A motor at one end rotates the holder to invert the extraction vessels end-over-end. The vessels shown are the same size and aligned the same way up. Little detail is given but several rotary agitation apparatuses are listed on page 11867 vol. 61 of the Federal Register together with their suppliers.

The inventive rotary agitation apparatus disclosed herein provides a solution to these problems. Broadly stated, this aspect of the invention provides a rotary agitation apparatus for rotating bottles about an axis which rotary agitation apparatus includes a plurality of bottle-holding devices each of which has a pair of radially movable gripping members for engaging and holding a bottle said gripping members being coupled together to be positioned symmetrically with respect to said axis during their movement so as to hold different size bottles approximately centered on said axis. Preferably, the gripping members are shaped to leave a zone in the vicinity of a radius perpendicular to the rotation axis free and clear for receipt of an appendage extending longitudinally from the bottle.

The axial centering of the bottles is effective not only in reducing any net centrifugal forces as the bottles are rotated, by balancing them, but also by centering the bottles, in reducing their rotational inertia and thence the torque required.

Also desirable is modularity of the structure. A single motor is capable of driving a considerable number of rotating bottles arranged along an axis. However, varying constraints of throughput, space and cost make a modular system desirable in which capacity for additional bottle rotator units can be added along the axis, as needed.

The inventive bottle-rotator disclosed herein includes simple and economic means for adding such units, preferably with capacity for two bottles per unit.

Further advantage in handling bulky bottles of substantial length, or encumbered with substantial appendages, is found by providing for lateral or side loading and removal of the bottles, lateral with respect to their length, that is. This desirable objective is also achieved by the bottle rotator of this invention.

The bottle rotator shown in FIGS. 4 to 6 is a bench-top model and comprises a rectangular frame 100 for a pair of bottles such as the one shown at 102, which frame is externally journalled in bearing pieces 104 which support the frame 100 for rotation about a rotation axis extending through the mid-points of shorter side pieces 106. Bearing pieces 104 are bolted to trestles 108 each of which has a pair of spreading legs 110 connected at their lower ends to cross pieces 112 and base runners 114.

The frame 100 is rotated by a motor 116 through a chuck or coupling 118 on a drive shaft 120 extending through left-hand bearing 104. A stub axle 122, or trunnion, supports the right-hand side piece 106 of frame 100 to idle in right-hand bearing 104. Preferably for modularity, stub axle 122 comprises a half-cut trunnion that can interengage with a second such trunnion on the other side of bearing 104 to transmit drive to that second trunnion.

Motor 116 is supported on a motor table 124 carried by left-hand trestle 108 and by a pair of motor table legs 126 anchored to base runners 114. The motor 116 and drive train as well as the bottle 102 are omitted from FIG. 5, for clarity.

Frame 100 carries a pair of bottle clamping or gripping structures and the whole assemblage is symmetrical on either side of the rotation axis. Thus, the frame 100 comprises a pair of cross-members 128 mounted across the ends of side pieces 106. Cross-members 128 are each sinuous in plan (FIG. 5), with a flange-like construction for strength, a first V-section 130 opening in one direction, a second V-section 132 opening in the opposite direction and a bulkhead 134 supported between the V-sections 130 and 132.

Extending between the bulkheads 134 are a pair of guide posts 136 and a pair of rotatable threaded shafts 138. Each shaft 138 is equipped with a handwheel 140, one above and one below the frame 100, as viewed in FIG. 4. The guide posts 136 are axially displaced a small distance either side of a center line of the frame 100 while the threaded shafts 138 are displaced a small distance transversely of the rotation axis, also on either side thereof. Each shaft 138 carries an external left-hand thread along one end or half and a right-hand thread along the other end or half. These opposed threads can nearly meet in the middle, like a turnbuckle. For symmetry and convenience, as well as for a compact construction, the hand wheels 140 are at opposite sides of the frame 100, and lie outside it.

Riding on the guide posts are two pairs of sliders 142 each engaging one of the threaded shafts 138 to be driven along the shaft 138 when the shaft is rotated. For this purpose, each slider 142 has a threaded opening and does not need to extend all around the shaft 138, but should engage at least half its circumference. The four sliders 142 extend outwardly across the frame 100 away from the guide posts 136 in opposite directions and each has two openings through which the guide posts 136 pass to stabilize the sliders 142 against rotation about the threaded shafts 138.

Each slider 142 carries a bottle clamping or gripping member configured to engage the bottle or other object mounted in the frame and to hold it securely between a pair of opposed clamping members. The clamping members can be shaped to conform to the outer surfaces of the rotated object. As shown in the drawings, each clamping member is in the form of a circular clamp plate 144 having a substantial cutout 146, which as shown is in the form of a wide radial slot extending to the center of each clamp plate 144, and serves to accommodate protrusions or extensions of bottles or zero-headspace extractors 102. As shown, a thumbscrew 52 can extend through the cutout 146. The cutouts 146 open in the same direction as the V-shaped openings 130 or 132 and these structures cooperate to provide clearance for such extensions past the limits of the frame 100.

The clamp plates 144 lie in opposed pairs on either side of the threaded shafts 138 providing two bottle-receiving bays, one on each side.

Rotation of a hand wheel 140 moves two members of a pair of clamp plates 144 towards or away from each other, in tandem. In the preferred embodiment disclosed herein, the clamp plates 144 are equidistant from the axis of rotation through the bearings 104, and this disposition is maintained throughout their travel, so that an object clamped between them is centered on the rotation axis between the clamp points. To facilitate their gripping function, the clamp plates 144 can be surfaced with rubber or other friction material or pads. By this means, a variety of different objects can easily be securely clamped between a pair of clamp plates 144 turning a hand wheel 140. Clearly the size of the object, bottle or zero-headspace extractor that can be accommodated is determined by the size of the frame 100 and the limits of travel of the clamp plates 144.

A bottle or other object, in this case a zero-headspace extractor such as that shown in FIG. 2, can conveniently be loaded with the frame 100 in an upright generally vertical position, and the cutouts 146 facing forwardly, as shown on the left-hand side of FIG. 4. The frame 100 can readily be rotated to remove the zero-headspace extractor 102 on the right-hand side, or the zero-headspace extractor can be removed or replaced from the far side or back of the apparatus. This side-loading feature of the inventive bottle rotator is an important convenience for relatively bulky objects, especially long ones, that can be difficult to load vertically. Also, the left- and right-hand bays can be loaded and unloaded quite independently, being provided each with their own clamping or securing mechanism carried by the frame 100, enabling different-sized bottles to be loaded side-by-side, each centered on the axis of rotation, within the same frame 100.

Once loaded to the frame 100 one or two bottles are rotated end-over-end by actuating the motor 116. The symmetry of the rotating parts of the apparatus combined with the centering of objects on the axis of rotation serves to reduce or minimize the load on the motor.

A single motor 116 is thus able comfortably to rotate a considerable number of bottles or zero-headspace extractors 102. For this reason, the apparatus is designed to be modular, providing for the addition of one or more further frames 100 with support trestles 108 along the axis of rotation, drive means being provided to transmit the rotary drive from one frame to the next.

Figure 9:
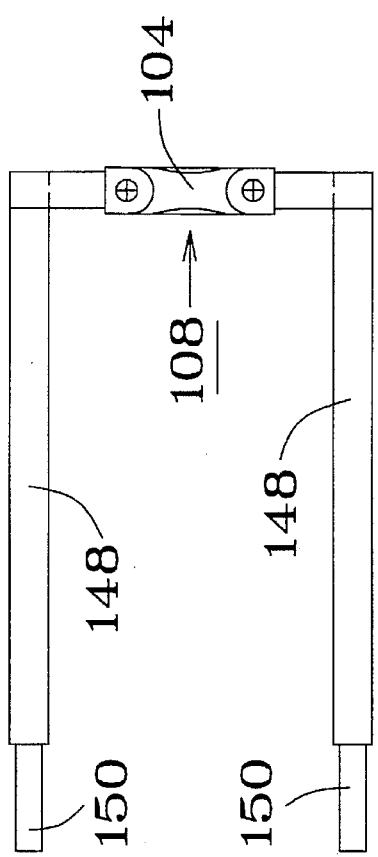
FIG. 9 is a top plan view of the expansion base of FIG. 7.
Figure 8:
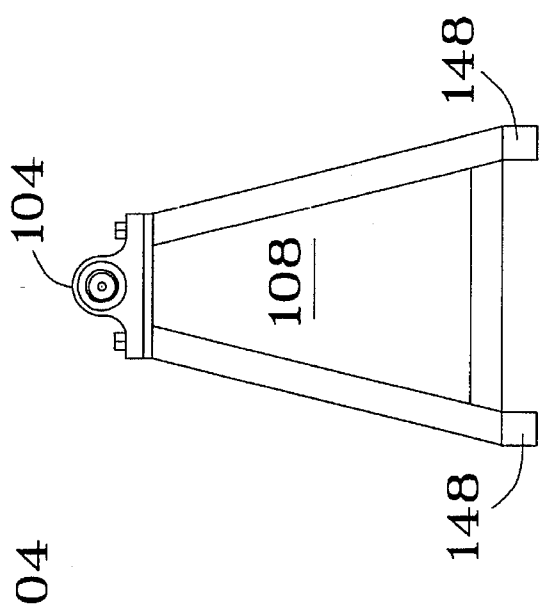
FIG. 8 is a right-hand end elevational view of the expansion base of FIG. 7.
Figure 7:
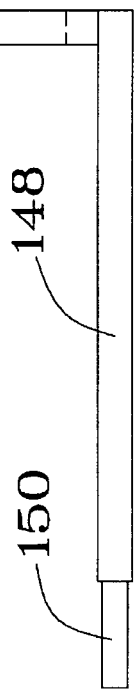
FIG. 7 is a side elevational view of an expansion base for the rotary agitation apparatus of FIG. 4.

The apparatus of FIGS. 7 to 9 shows one means for achieving modularity. A trestle 108, carrying a bearing 104, is attached at its feet to a pair of extension runners 148 to provide an extension base. The free ends 150 of the extension runners 148 are reduced to peg into sockets (not shown) in the runners 114. Similar sockets can conveniently be provided in the extension runners 148 to receive a further extension base. A further frame 100 can be mounted on or assembled with such an extension base, while the extension base itself is being assembled with the bottle rotator of FIGS. 4 to 6. As indicated above, the frames 100 can have interengageable stub axles 122 to transmit rotation from one frame to the next, at bearing 104. As many as four or six such extensions, or more, can be assembled in line, if desired, depending upon the need and the space available.

As stated previously, the trestles 108 and the table legs 126 are designed to provide a bench top apparatus. If desired they can be longer to provide a floor model, similar considerations applying also to the extension base shown in FIGS. 7 to 9. Clearly the length of bottle extension that can be accommodated will depend upon the clearance between frame 100 and base runner 114.

It should be noted that the two bottle-receiving bays defined within the frame 100 face in opposite directions for balancing similar, irregularly shaped objects and for loading convenience.

The bottle rotator disclosed in FIGS. 4 to 6 provides an efficiently constructed apparatus for rotating the novel, lightweight zero-headspace extractors disclosed with reference to FIGS. 1 to 3. A number of pairs of such extractors can be agitated simultaneously using one or more of the extension bases shown in FIGS. 7 to 9 together with an appropriate number of frames 100 and the clamping apparatus carried by the frames 100.

While a variety of construction materials can of course be used, a preferred material for the frame 100 is steel while the sliders 142 and the clamp plates 144 can be formed of aluminum alloy or plastic, for lightness.

The terminology used herein is intended to be consistent with that used in the Federal Register, and in case of doubt, the usage of the Federal Register should be applied herein. In particular, the term "solid" material, as discussed in the Federal Register, is used to include semi-solid and paste-like materials that do not pass through the filtration means.

While an illustrative embodiment of the invention has been described above, it is, of course, understood that various modifications will be apparent to those of ordinary skill in the art. Such modifications are within the spirit and scope of the invention, which is limited and defined only by the appended claims.

We claim:

1. A pressurizable zero-headspace extractor vessel useful in preparing multiphase sample mixtures for constituent analysis, said constituents potentially including heavy metals and volatile organics and said sample mixtures comprising solid-phase material and liquid-phase material, said liquid-phase material including an extraction liquid, wherein said extractor vessel is agitatable to effect thorough mixing of said sample mixture and comprises:

a) a cylinder;
   b) a pressurizable sample chamber for said multiphase sample mixtures, within said cylinder, said sample chamber being pressurizable to a working pressure of at least 50 psig;
   c) a discharge port for egress of liquids from said sample chamber;
   d) a piston movable in said cylinder to pressurize said sample chamber and drive fluids out of said discharge port;
   e) piston-driving means to urge said piston to move in said cylinder;
   f) solids-retaining filtration means to retain solid-phase material within said sample chamber as fluids are driven out;
   g) liner members defining said pressurizable sample chamber, said liner members having wettable surfaces in said sample chamber, said wettable surfaces constituting the surfaces contacted by said sample mixtures during normal use of said vessel, said liner members and wettable surfaces being formed of a fluorinated polymer selected from the group consisting of fluorinated polymers and copolymers of alkylenes and alkoxylenes and fluorinated polymers and copolymers of chlorinated alkylenes and alkoxylenes;
   h) structural support members defining said cylinder backing and supporting said liner members to sustain said substantial working pressure in said sample chamber, said structural support member being formed of a lightweight structural material selected from the group consisting of polypropylene, high-density polyethylene, poly vinyl chloride, and copolymers of any one of these polymers; and
   i) sealing means between said liner members, said sealing means being operative to seal said fluorinated polymer liner members to retain said working pressure of at least 50 psig;

whereby samples can be admixed and agitated with an extraction liquid in said sample chamber, under said working pressure, and said admixed extraction liquid can be discharged from said vessel for testing, while said sample mixtures contact only said wettable surfaces of said extractor vessel, said wettable surfaces being formed of said fluorinated polymer material.

2. A vessel according to claim 1 wherein said fluorinated polymer is polytetrafluoroethylene.

3. A vessel according to claim 1 wherein said inert material is polytetrafluoroethylene.

4. A vessel according to claim 1 wherein said structural members provide a casing extending generally around said sample chamber to provide three-dimensional support for said wettable surfaces.

5. A vessel according to claim 1 wherein said structural members comprise a tubular shell embracing said cylinder and end caps, one end cap engaging each end of said shell and extending over said ends of said cylinder.

6. A vessel according to claim 1 comprising manually operable screw means to urge said piston, to pressurize said sample chamber.

7. A vessel according to claim 1 comprising pneumatically actuated means to urge said piston, to pressurize said sample chamber.

8. A vessel according to claim 1 wherein said pneumatically operable means comprises a pressure chamber on the opposite side of said piston facing away from said sample chamber, and a pneumatic end cap having means to admit pressurized gas to said pressure chamber through said end cap.

9. A vessel according to claim 8 wherein said pneumatic end cap is equipped with an air connector opening and has a raised central circular land provided with a peripheral recess in which an O-ring seal is seated to maintain gas pressure behind said piston.

10. A vessel according to claim 1 comprising a separable liner bearing said wettable surfaces in said sample chamber, said separable liner being removable from said supporting structural member.

11. A vessel according to claim 1 comprising a closing member for said cylinder, said closing member and said piston being opposed to define said sample chamber within said cylinder, wherein said closing member comprises an end flange extending across said cylinder and an outwardly opening passageway extending from said end flange and providing said discharge port, said end flange and said passageway comprising at least one of said fluorinated polymer liner members and comprising one of said support members whereby said end flange and said passageway are lined with fluorinated-polymer, wettable surfaces to said sample mixture and to egressing fluids, and said wettable surfaces are structurally supported to retain said working pressure within said sample chamber.

12. A vessel according to claim 11 wherein said support members comprise a sleeve for said cylinder and a ported end cap for said closing member, said sleeve and end cap being mutually threaded to close together with relative movement in a direction lengthwise of said cylinder.

13. A vessel according to claim 12 wherein said cylinder has an enlarged end portion to receive said end flange liner member and to receive said filtration means, said end cap extending over said end flange liner and said enlarged end portion of said cylinder, whereby closure of said end cap and sleeve is effective to clamp said end flange against said filtration means in said enlarged end portion.

14. A vessel according to claim 13 comprising facing cylindrical surfaces on said enlarged cylinder portion and said end flange and a ring seal between said cylindrical surfaces, wherein said end cap extends around and, in a cylindrically lengthwise direction, past said seal whereby closing said end cap on said sleeve clamps said seal.

15. A vessel according to claim 1 wherein said piston comprises one of said liner members and one of said support members backing said piston liner member, said piston liner member comprising a continuous disk occluding said cylinder transversely.

16. A vessel according to claim 15 wherein said piston liner member carries a plurality of sealing rings, and said cylinder support member has a thickened structure providing dimensional stability for slidable sealing of said piston in said cylinder.

17. A vessel according to claim 16 wherein said piston-driving means comprises a manually operable screw member mounted on said cylinder, and said support member backing said piston liner member is adapted for engagement with said manually operable screw member to be movable therewith in both advance and retraction directions.

18. A vessel according to claim 1 wherein said structural members provide a casing extending generally around said sample chamber to provide three-dimensional support for said wettable surfaces and comprise a tubular shell embracing said cylinder and end caps, one end cap engaging each end of said shell and extending over said ends of said cylinder.

19. A pressurizable zero-headspace extractor vessel useful in preparing multiphase sample mixtures for constituent analysis, said constituents potentially including heavy metals and volatile organics and said sample mixtures comprising solid-phase material and liquid-phase material, said liquid-phase material including an extraction liquid, wherein said extractor vessel is agitatable to effect thorough mixing of said sample mixture and comprises:

a) a cylinder;

b) a pressurizable sample chamber for said multiphase sample mixtures within said, cylinder, said sample chamber being pressurizable to a working pressure of at least 50 psig;

c) a discharge port for egress of liquids from said sample chamber;

d) a piston movable in said cylinder to pressurize said sample chamber and drive fluids out of said discharge port;

e) piston-driving means to urge said piston to move in said cylinder;

f) solids-retaining filtration means to retain solid-phase material within said sample chamber as fluids are driven out;

g) liner members defining said pressurizable sample chamber, said liner members having wettable surfaces in said sample chamber, said wettable surfaces constituting the surfaces contacted by said sample mixtures during normal use of said vessel, said liner members and wettable surfaces being formed of a fluorinated polymer selected from the group consisting of fluorinated polymers and copolymers of alkylenes and alkoxylenes and fluorinated polymers and copolymers of chlorinated alkylenes and alkoxylenes;

h) structural support members defining said cylinder backing and supporting said liner members to sustain said substantial working pressure in said sample chamber, said structural support member being formed of a lightweight, moldable, synthetic-polymer plastic structural material said structural material is a plastic selected from the group consisting of polypropylene, high-density polyethylene, poly vinyl chloride, copolymers of any one of the foregoing polymers, ultra-high molecular weight polyethylene, chlorinated polyvinyl chloride, acrylonitrile butadiene styrene copolymer, polyvinylidene fluoride and polyacetal plastics polymers; and i) sealing means between said liner members, said sealing means being operative to seal said fluorinated polymer liner members to retain said working pressure of at least 50 psig;

whereby samples can be admixed and agitated with an extraction liquid in said sample chamber, under said working pressure, and said admixed extraction liquid can be discharged from said vessel for testing, while said sample mixture contact only said wettable surfaces of said extractor vessel, said wettable surfaces being formed of said fluorinated polymer material.

* * * * *